United States Patent [19]

Sprague

[11] Patent Number: 4,479,791
[45] Date of Patent: Oct. 30, 1984

[54] TAMPON APPLICATOR
[75] Inventor: E. Russell Sprague, Monson, Mass.
[73] Assignee: Tampax Incorporated, Lake Success, N.Y.
[21] Appl. No.: 491,784
[22] Filed: May 9, 1983

Related U.S. Application Data

[63] Continuation of Ser. No. 172,556, Jul. 28, 1980, abandoned.

[51] Int. Cl.$^3$ .............................................. A61F 15/00
[52] U.S. Cl. ...................................... 604/14; 604/16; 604/18
[58] Field of Search ...................... 604/11, 14, 15, 16, 604/18

[56] References Cited

U.S. PATENT DOCUMENTS

| | | | |
|---|---|---|---|
| 2,832,342 | 4/1958 | Wingenroth | 128/263 |
| 3,090,385 | 5/1963 | Brecht | 128/263 |
| 3,101,713 | 8/1963 | Sargent | 128/263 |
| 3,766,921 | 10/1973 | Dulle | 128/270 |
| 4,273,125 | 6/1981 | Sakurai | 128/263 |
| 4,276,881 | 7/1981 | Lilaonitkul | 128/263 |
| 4,286,595 | 9/1981 | Ring | 128/263 |

Primary Examiner—C. Fred Rosenbaum
Assistant Examiner—Sherri E. Vinyard
Attorney, Agent, or Firm—Curtis, Morris & Safford

[57] ABSTRACT

A tampon applicator of the telescoping tube type including an ejector tube adapted to store a tampon in its distal end, a plurality of fingers formed in said distal end, an outer tube slip fit over the ejector tube, directionally-locking inward projections fixed within the distal end of said outer tube so as to pass between said fingers and engage a tampon carried therein thus securing the latter relative to said outer tube while permitting only distal expulsion therefrom. Said applicator charged with a tampon is packaged and stored in a telescopically collapsed position. It is activated for use by partial withdrawal of the ejector tube from the outer tube until the fingers of the ejector tube pass beyond the tampon and catch behind the proximal end of said tampon. The applicator is then used in the usual manner by telescopically collapsing the ejector tube into the outer tube, whereby the ejector tube serves as a plunger bearing against the proximal end of the tampon to expel the latter.

Said outer tube preferably has inwardly curving protective petal sections at its distal end which form a rounded tip for facilitating insertion yet yieldably pass the tampon therethrough during the ejection step.

1 Claim, 13 Drawing Figures

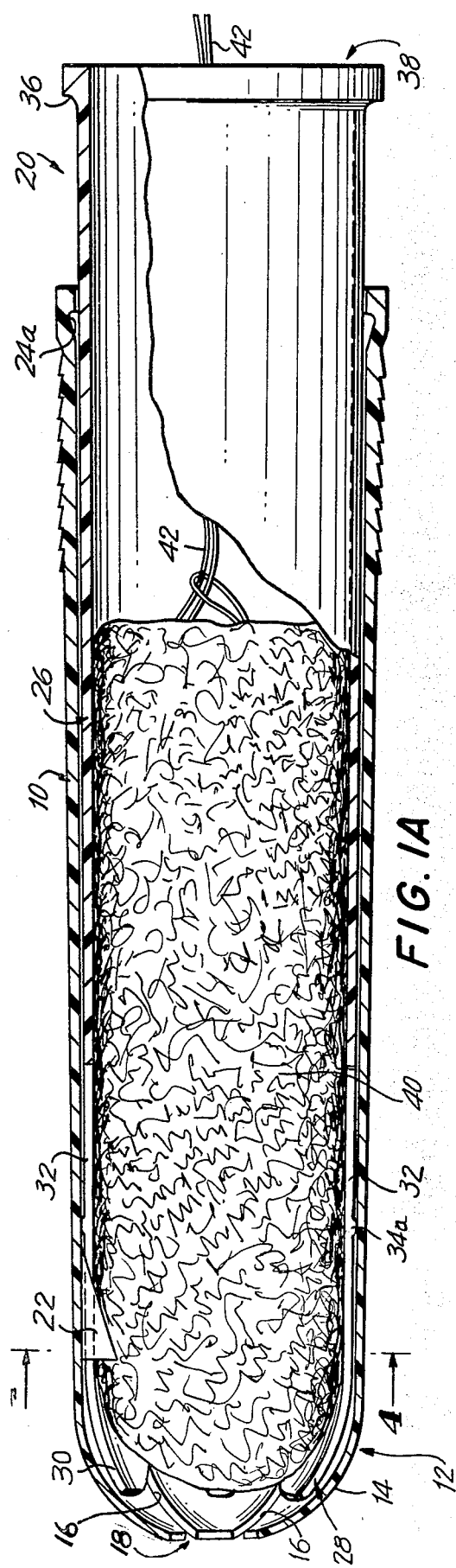
FIG. 1A
FIG. 1B
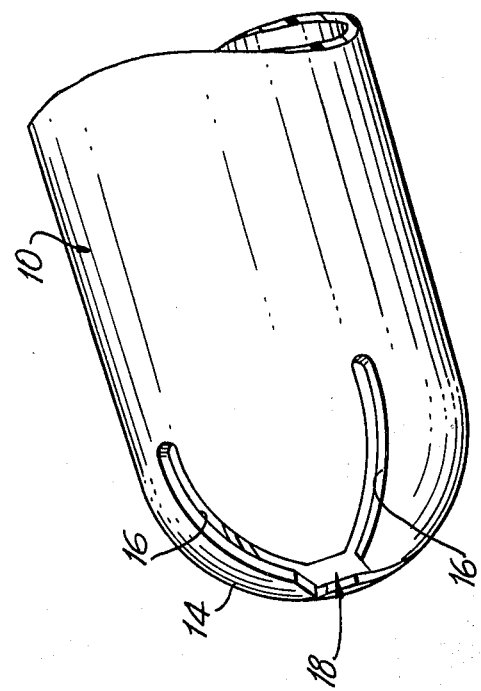
FIG. 2

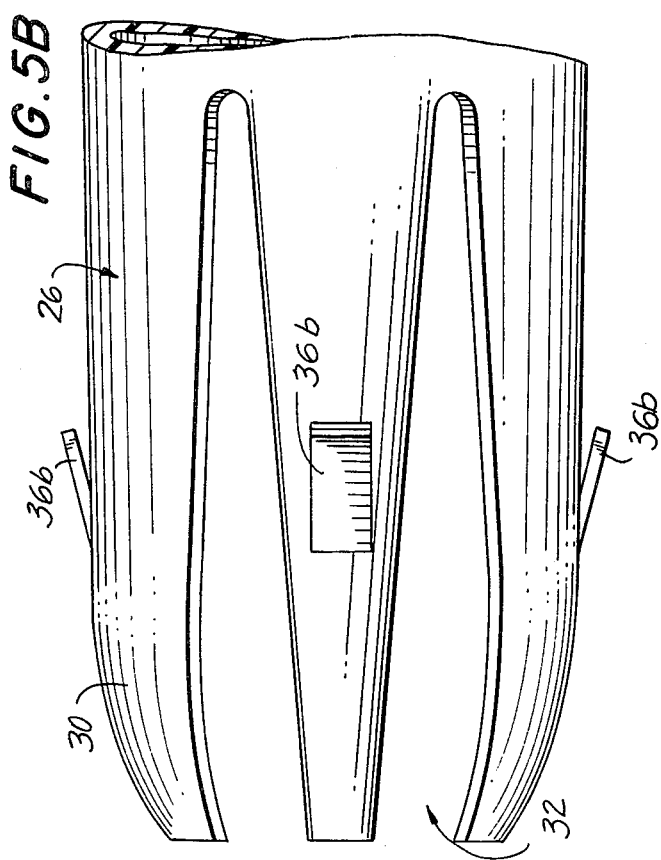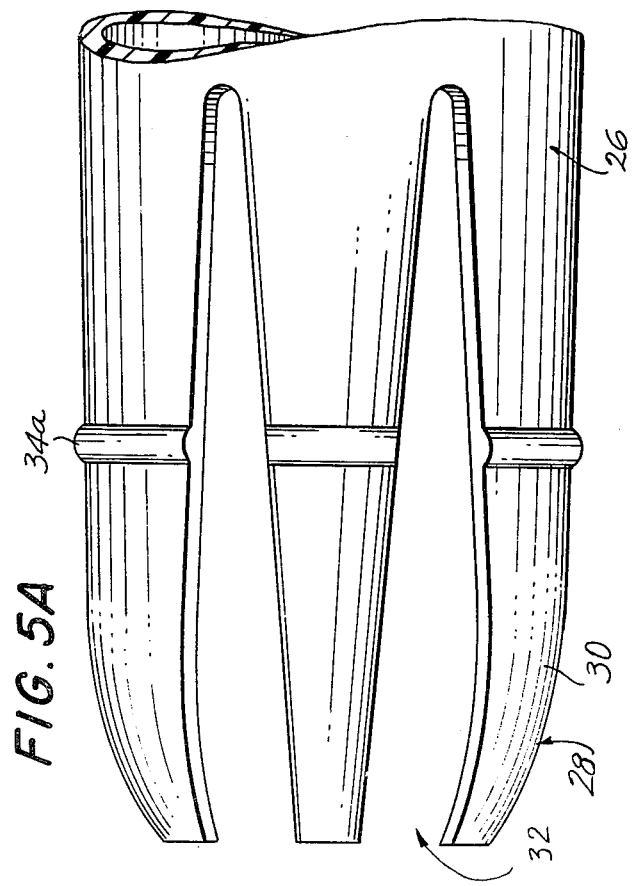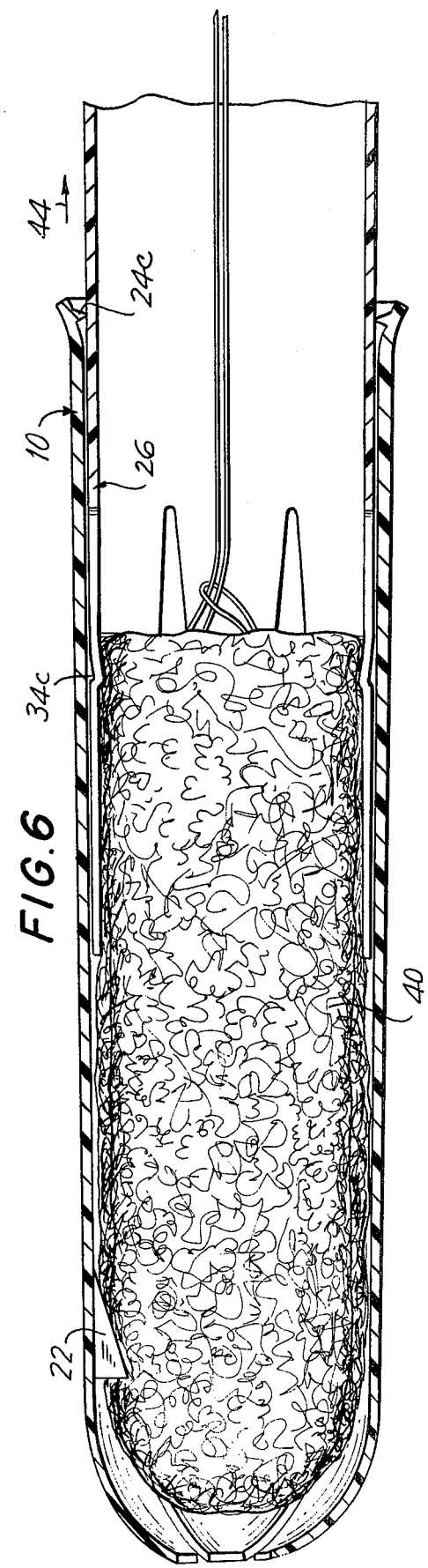

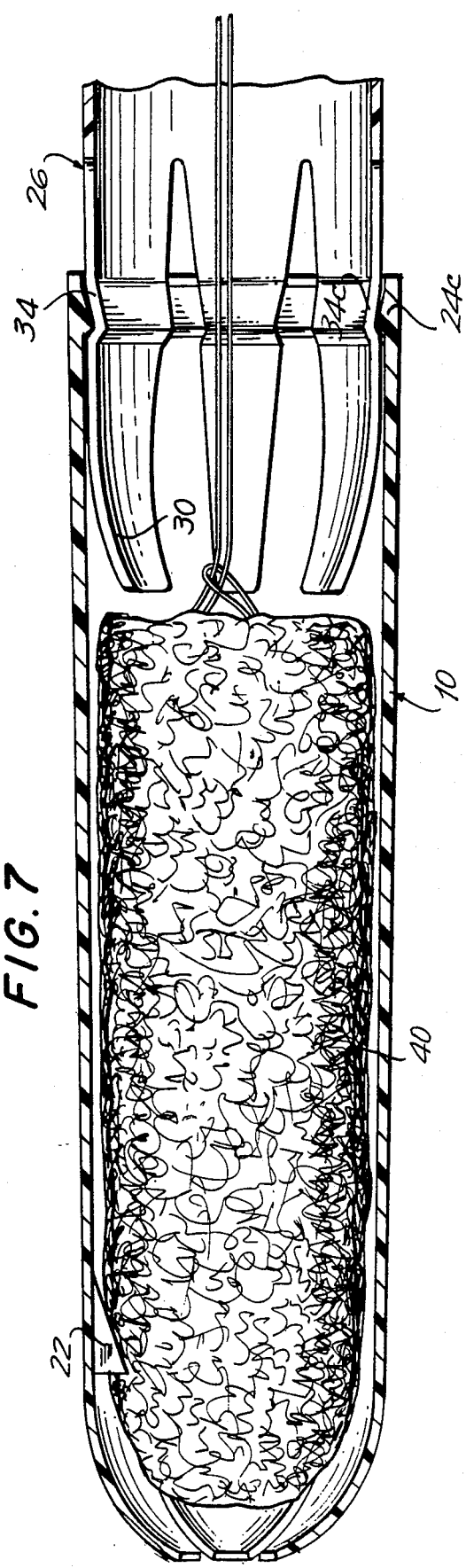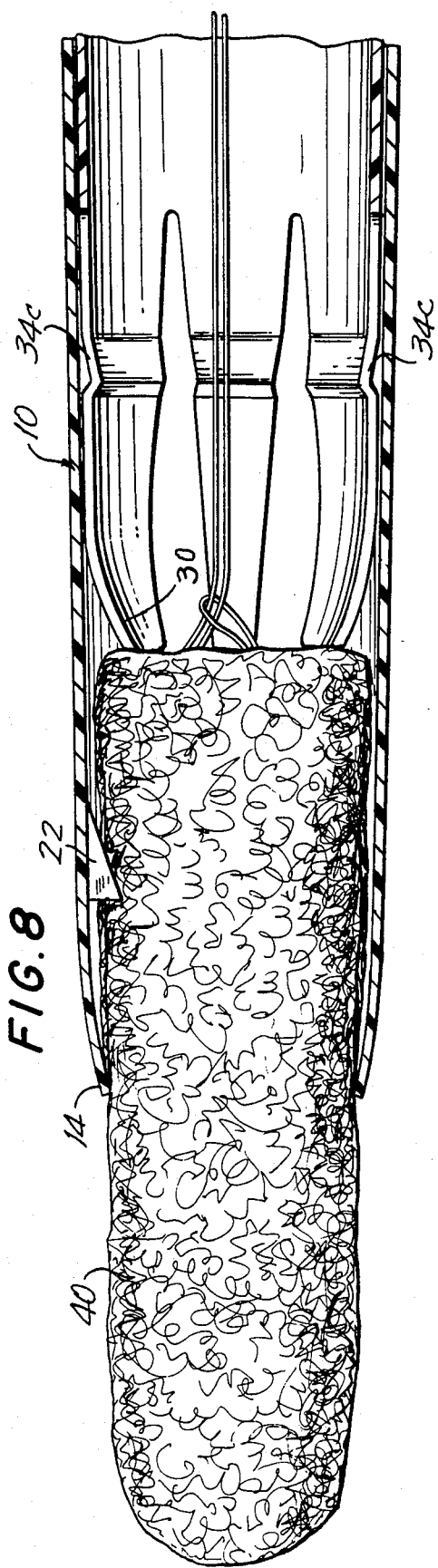

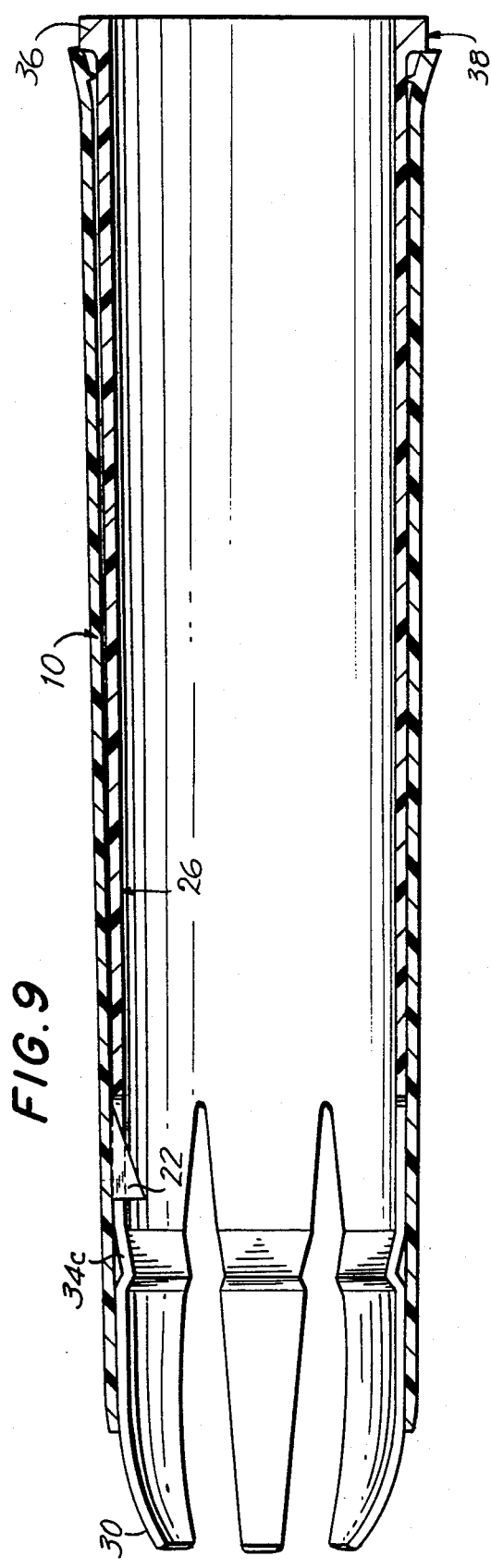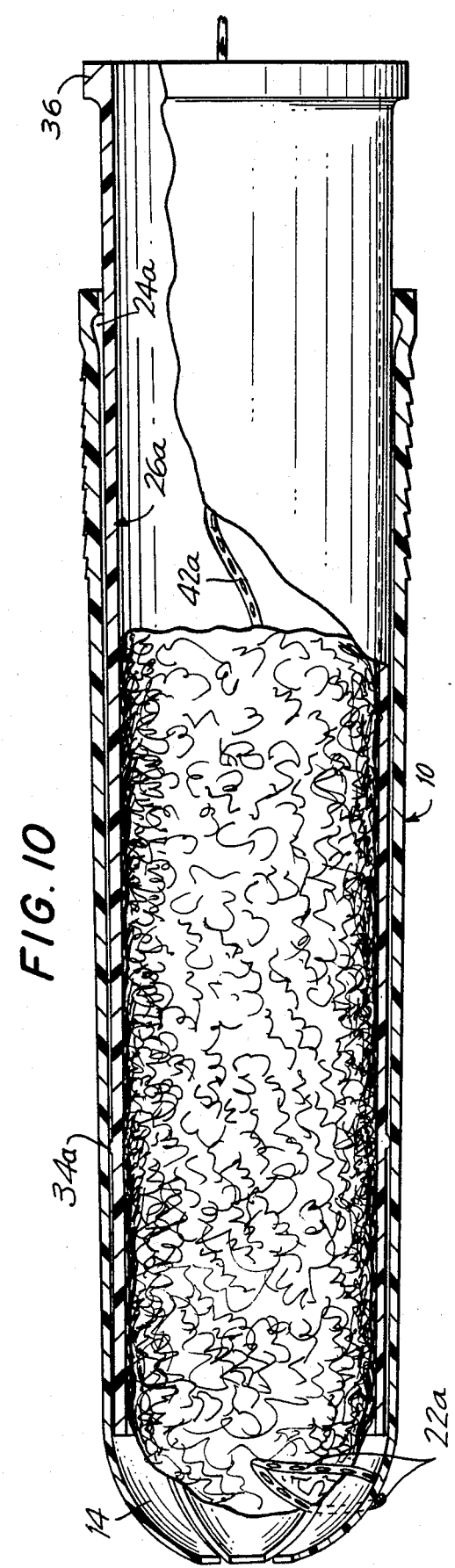

TAMPON APPLICATOR

This application is a continuation of application Ser. No. 172,556, filed July 28, 1980, now abandoned.

BACKGROUND OF THE INVENTION

This invention relates to tampon applicators and, more particularly, is directed to tubular catamenial tampon applicators of the telescoping type.

Most currently available tampon applicators for introducing catamenial tampons intravaginally consist of a pair of telescoping tubes. The outer tube is designed to store a tampon at one end. The inner or ejector tube is slightly smaller in diameter and is slidably positioned behind the tampon carried in the outer tube. In use, the tampon is ejected from the applicator by pushing the inner tube into the outer tube to expel the tampon.

Several drawbacks are associated with such applicators for certain uses. For example, such tampon applicators are substantially longer than the tampons. First, the outer tube must be of a length sufficient to assure proper depth of insertion. Next, when the tampon and outer tube are assembled with the ejector tube, a major portion of the latter tube necessarily extends out from the end of the outer tube. This results in the over-all length of the packaged ready-for-use tampon applicator being approximately two and one-half times the length of the tampon. As a result of such a relatively large size, the bulk and cost of the packaging for such applicators are increased.

Women commonly carry such packaged tampons (with applicators) in their purses. Because of the length of such applicators, they occupy a relatively large amount of space in the purse. It is therefore also desirable to produce a tampon applicator of smaller size which is less obtrusive. This is a particular problem for younger women who often prefer not to carry purses and with today's fashions often must use pockets in relatively tight-fitting clothes.

One type of tampon applicator which has sought to solve the above problems has utilized a substantially flat, elongated plunger arm which is stored positioned along the outside of and in longitudinal alignment with the outer tube. See U.S. Pat. Nos. 3,059,641; 3,059,642; 3,103,929; 3,115,876; and 3,759,258. This type of applicator has apparently never been commercialized.

OBJECTS AND SUMMARY OF THE INVENTION

Accordingly, it is an object of this invention to provide a tampon applicator that overcomes the above-described difficulties.

More particularly, it is an object of this invention to provide a tampon applicator which is compact and of reduced size.

It is another object of this invention to provide a tampon applicator which is simple in construction and convenient and easy to use.

It is still another object of this invention in an alternative preferred embodiment to provide a tubular tampon applicator of the telescoping type which is capable of positioning a tampon intravaginally with greater accuracy and reliability, without frictional irritation, and yet without increasing the standard size of the tube.

In accordance with a preferred embodiment of this invention, a tampon applicator includes an ejector tube adapted to store a tampon therein. An outer tube is slidably disposed over the ejector tube. The outer tube is adapted to pass the tampon through its distal end during an ejection operation. Directionally locking inward projections are associated with the outer tube for engaging the tampon to prevent its movement in the rearward direction. Thus, when the ejector tube is partially withdrawn from the outer tube so as to be positioned behind the tampon, the projections fix the tampon relative to the outer tube. However, when the ejector tube is forced back into the outer tube so as to eject the tampon therefrom, the projections permit the forward displacement and expulsion of the tampon.

In a further preferred embodiment of this invention, the ejector tube has fingers at its distal end. These are adapted to slide over the tampon upon withdrawal of the ejector tube and automatically to close inwardly behind the tampon sufficiently to engage the end of the latter. Also projections preferably may comprise inclined ramps formed on, and attached to, the inside of the outer tube at or near its distal end. These projections extend through open-ended slots between the fingers of the ejector tube so as to engage the tampon.

In this specification and the accompanying drawings, I have shown and described a preferred embodiment of my invention and have suggested various alternatives and modifications thereof, but it is to be understood that these are not intended to be exhaustive and that many other changes and modifications can be made within the scope of the invention. These suggestions herein are selected and included for purposes of illustration in order that others skilled in the art will more fully understand the invention and the principles thereof and will thus be enabled to modify it and embody it in a variety of forms, each as may be best suited to the conditions of a particular use.

BRIEF DESCRIPTION OF THE DRAWINGS

FIG. 1A is a longitudinal view partially in cross-section of a preferred embodiment of a tampon applicator according to this invention;

FIG. 1B is an enlarged detail of an alternative embodiment of a portion of the restraining means shown in FIG. 1A;

FIG. 2 is a perspective view of the distal end of the outer tube shown in FIG. 1A;

FIG. 5A is a side view of the distal end of the ejector tube shown in FIG. 1A;

FIGS. 5B and 5C are similar to FIG. 5A, but showing alternative embodiments of a portion of the restraining means;

FIGS. 6, 7, 8, and 9 are each a cross-sectional view of the tampon applicator of FIG. 5C, respectively showing: the ejector tube being withdrawn from its stored position within the outer tube towards its operative position; showing the ejector tube positioned ready to start the ejection operation; showing the ejector tube expelling the tampon from the outer tube; and showing the position of the ejector tube at the completion of the ejection operation; and FIG. 10 is a view similar to FIG. 1A of an alternative preferred embodiment showing a different gripping means.

DETAILED DESCRIPTION OF THE PREFERRED EMBODIMENT

Figure 4:
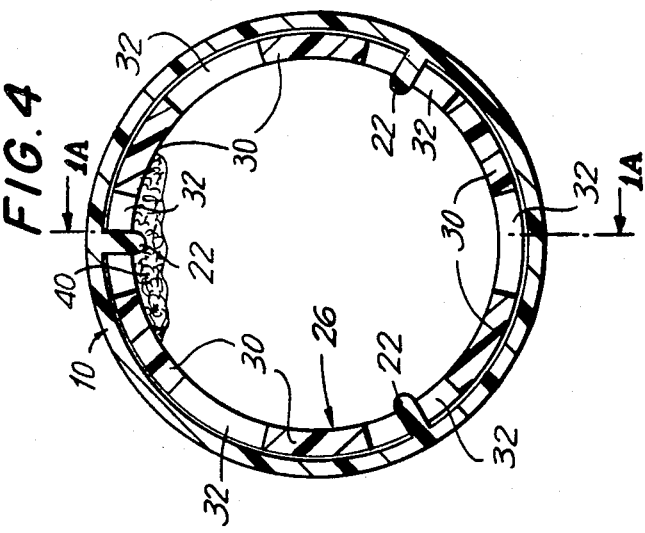
FIG. 4 is a cross-sectional view of the tampon applicator of FIG. 1A, taken along lines 4—4 thereof.
Figure 3:
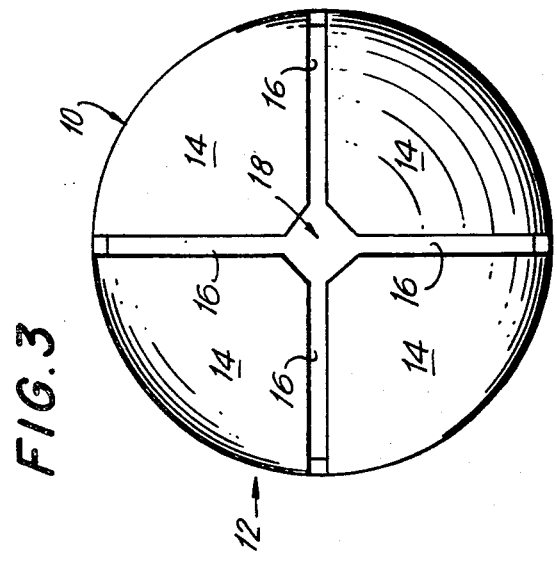
FIG. 3 is a distal end view of the tampon applicator of FIG. 1A.

Referring to FIG. 1A, the tampon applicator comprises a cylindrical outer tube 10. This is preferably formed at its distal end 12 with petal sections 14 which are separated from each other by respective slots 16 (FIG. 2). Petal sections 14 are made relatively flexible and normally biased in a substantially arcuate closed configuration to form a rounded tip having a central opening 18 at distal end 12 (as shown in FIGS. 1A and 2). This rounded shape of the distal end 12 is useful to facilitate the insertion of the applicator into the vaginal cavity. Accordingly, outer tube 10 is preferably constructed from any suitable smooth plastic material by molding by a conventional forming process. The opposite or proximal end 20 of outer tube 10 is open.

Outer tube 10 further includes a plurality of inward projections 22 preferably secured along an inner circumferential portion thereof. Projections 22 in the illustrated preferred embodiment are of a substantially flat right triangular configuration (FIG. 1A) with the long side thereof extending at an acute angle from the inner wall of outer tube 10 towards central opening 18. Projections 22 extend far enough into the center of outer tube 10 to engage a catamenial tampon disposed therein. Although three projections 22 are shown in FIG. 4 for engaging the tampon, this number may vary as desired. These projections 22 are preferred, because this configuration is more tolerant of variations in the diameter of the tampon 40. Additional projections would give more positive engagement of the tampon, but would make it more difficult to expel. Outer tube 10 is further shown to include an annular groove 24a along an inner circumferential portion of proximal end 20.

Figure 5C:
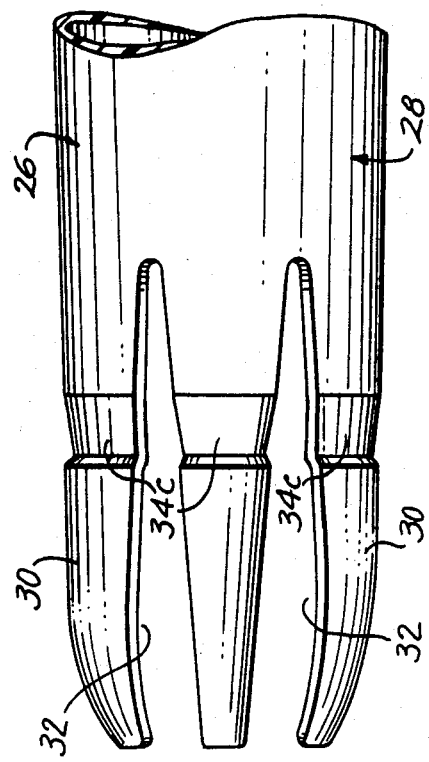

The tampon applicator illustrated in FIG. 1A further comprises an inner or ejector tube 26. This serves as a plunger for ejecting a tampon positioned within the distal end of outer tube 10. Ejector tube 26 is dimensioned to slidably move within outer tube 10, preferably with minimal clearance therebetween. Ejector tube 26 is also slightly longer than outer tube 10 to assure complete ejection of the tampon 40. Referring to FIG. 5A, it is seen that the distal end 28 of ejector tube 26 is preferably formed with a plurality of fingers 30 which are separated from each other by slots or openings 32 through which the projections 22 of outer tube 10 extend to engage the tampon 40 disposed therein. Although the number of fingers 30 and slots 32 may vary as desired, six slots 32 are shown in FIG. 4 for ready alignment with the three projections 22 also shown therein. In the same manner as with petal sections 14 of outer tube 10, fingers 30 are made so as to be slightly biased towards a closed configuration, as shown in FIGS. 1A and 5A.

In order to limit the axial movement of inner tube 26 relative to outer tube 10, each finger 30 further includes a raised detent or rib 34a to coact with the groove 24a. Ejector tube 26 also preferably includes an outwardly directed circumferential retention flange 36 at its proximal end 38.

Referring to FIG. 1A, the tampon applicator according to this invention is shown in its stored configuration, ready for packaging, with ejector tube 26 being disposed almost entirely without outer tube 10. A tampon 40 is stored within ejector tube 26, not directly in the outer tube. The tampon is comprised of an absorbent material formed into the general shape of an elongated cylinder and having attached to its rearward portion a withdrawal string 42, as is conventional in the art. For example, withdrawal string 42 may be doubled to form a loop locking the two loose ends. In this configuration, outer tube 10 is telescoped over ejector tube 26 with the distal ends of the two tubes being in substantial alignment and with projections 22 of outer tube 10 extending through respective openings or slots 32 between fingers 30 to engage tampon 40. It is thus readily apparent from FIG. 1A that the dimension of the tampon applicator in its stored configuration is approximately one and one-half times the length of tampon 40 in contradistinction to previously-described conventional telescoping tube devices having a length of two and one-half times that of the tampon stored therein. The length is now controlled only by the insertion depth desired (and not by the applicator design requirements).

In operation, outer tube 10 is firmly held while ejector tube 26 is partially withdrawn therefrom (i.e. ejector tube 26 is axially moved in the direction away from central opening 18, shown by arrow 44 in FIG. 6). During this activating step, tampon 40 remains in a fixed position relative to outer tube 10 by means of projections 22 which act like barbs gripping the tampon and restraining its movement in the rearward direction. The fingers 30 of the ejector tube 26 slide over tampon 40. Once fingers 30 are withdrawn past the proximal or rear end of tampon 40, they close toward each other so as to be positioned behind tampon 40 for the start of the ejection operation (see FIG. 7).

The tubes 10 and 26 of the applicator are prevented from becoming disessembled during the activating step by a restraining means 24 and 34 (the different embodiments thereof in the different drawings being respectively identified by letter suffix designation, e.g. 34a in FIG. 5A).

In the interlocking restraining means illustrated in FIGS. 6 to 9, a circumferential detent 24c rides upon the outer surface of ejector tube 26, causing the proximal end 20 of outer tube 10 to be slightly stressed in an outwardly radial direction (FIG. 9). However, when ejector tube 26 is positioned behind tampon 40, detent 24c mates with the sloped recess sections 34c on fingers 30, as shown in FIG. 7, resulting in ejector tube 26 being restrained from further movement in the rearward direction. This prevents ejector tube 26 from being completely withdrawn from outer tube 10.

A preferred embodiment of the restraining means is shown in FIGS. 1A and 5A (see grooves 24a and rib 34a). In another alternative embodiment, the annular groove 24b (see FIG. 1B) has a more angular configuration, to better catch on flaps 34b and coact therewith.

It is usually after the ejector tube 10 has been pulled out to its operative position that the outer tube 10 is placed in the vaginal cavity. Ejector tube 26 is then telescoped back into the outer tube 10 towards the distal end thereof, pushing tampon 40 through central opening 18 spreading open the yieldable petal sections 14 (see FIG. 8). Because of the nature of the unidirectional locking projections 22 (in the illustrated embodiment due to the inclined projection thereof toward central opening 18), tampon 40 is free to move in the distal direction.

The forward extent of travel of the ejector tube 26 through outer tube 10 is limited by circumferential flange 36 which abuts against the proximal edge of outer tube 10 (FIG. 9). Since ejector tube 26 is slightly longer than outer tube 10, the distal end of ejector tube 26 extends beyond the distal end of outer tube 10. This assures that the tampon 40 will be completely discharged into the vaginal cavity.

The ejector tube 26 can be functional without fingers 30, if the tampon 40 as made is sufficiently expansive to closely fit within the outer tube (to ensure positive engagement by the distal end of the ejector tube against the proximal end of the tampon during the ejection step).

Without slots 32 formed by fingers 30, the unidirectionally locking projections 22 still must engage the distal end of the tampon 40. To do so, the tampon 40 would be stored with its distal end extending slightly out from the distal end of the ejector tube.

The projections 22 could be replaced by an alternative unidirectional gripping means, such as a distal loop extension 22a of the withdrawal cord 42. See FIG. 10. With the loop 22a looped around one of the petals 14 of the outer tube 10, the tampon 40 is held against proximal movement, yet permits distal expulsion.

The present invention is also applicable to use in a modified preferred embodiment of essentially standard length. The applicant has discovered that considerable intravaginal discomfort can be experienced by certain individuals during the expulsion from the applicator of the dry tampon over the delicate tissues of the vaginal cavity. This abrasive insertion from the movement of the tampon relative to the vaginal surface is particular noticeable during periods of low menstrual flow. Use of lubricants on the tampon surface is not entirely satisfactory in overcoming this problem. Applicant has discovered that by elongating the outer tube sufficiently to enable placement of the tampon in its final position before expulsion from the applicator, this problem can be avoided.

Equally important is the more accurate placement of the tampon which this embodiment provides.

Rather than holding outer tube 10 while depressing ejector tube 26 therethrough in a plunger-like action, the elongated tampon applicator of this embodiment is inserted deeper into the vaginal cavity so that the tampon is carried to its correct final position. Then the ejector tube 26 is held stationary while outer tube 10 is slid back thereover towards proximal end 38. This gives a pull-type action for placing, rather than "ejecting", the tampon 40 in the vaginal cavity. Since the walls of the applicator tube 10 are much smoother than the surface of the tampon, the abrasion problem is essentially eliminated. By storing the tampon 40 in the distal end of the inner tube 26 (rather than directly in the outer tube 10 as in the prior art), the applicator need not be lengthened relative to the prior art in order to achieve an applicator capable of pull-type placement of the tampon.

There is also greater control over the positive and accurate placement of the tampon by use of the pull-type action (as contrasted with the plunger expulsion of the prior art). Plunger expulsion may result in the tampon being turned during positioning.

The few prior art attempts at developing pull-type applicators have not been satisfactory, see for example the complex and costly structure of the device taught by U.S. Pat. No. 4,048,998.

For ease of manufacture it may be desirable to have longitudinally extending mating fins and grooves respectively on the inner surface of the outer tube 10 and on the outer surface of the inner tube 26 for purposes of giving positive rotational alignment between the two tubes. This would help assure the assembly of the applicator so that the projections 22 align with and extend into the slots 32.

What is claimed is:

1. A catamenial tampon applicator comprising:
   an ejector tube adapted to store a tampon therein, the distal end of said ejector tube comprising a plurality of spaced apart fingers;
   an outer tube slidably disposed over said ejector tube and having a distal discharge end;
   gripping means associated with said outer tube for engaging a tampon carried in said ejector tube so as to resist movement of such a said tampon towards the proximal end of said outer tube while permitting discharge of such a tampon from said distal end; and
   restraining means for preventing the disassembly of said ejector tube from said outer tube including a circumferentially extending raised detent means and a mating circumferential groove, respectively formed on the outer distal surface of said ejector tube and on the inner proximal end of said outer tube, said detent means being formed as a series of annularly extending raised ribs formed on the outside of the fingers of said ejector tube and said groove being formed on the inner surface of said outer tube adjacent its proximal end.

* * * * *